United States Patent [19]

Ichikawa

[11] Patent Number: 4,506,033

[45] Date of Patent: Mar. 19, 1985

[54] PROCESS FOR PRODUCING OXYGEN-CONTAINING HYDROCARBON COMPOUNDS

[75] Inventor: Masaru Ichikawa, Yamato, Japan

[73] Assignee: Sagami Chemical Research Center, Tokyo, Japan

[21] Appl. No.: 517,990

[22] Filed: Jul. 29, 1983

Related U.S. Application Data

[63] Continuation of Ser. No. 348,193, Feb. 12, 1982, abandoned, which is a continuation of Ser. No. 165,005, Jul. 1, 1980, abandoned.

[30] Foreign Application Priority Data

Jul. 3, 1979 [JP] Japan .................................. 54-83521
Oct. 3, 1979 [JP] Japan ................................ 54-126823

[51] Int. Cl.$^3$ .............................................. C07C 27/06
[52] U.S. Cl. ..................................... 518/716; 518/714
[58] Field of Search ................................ 518/714, 716

[56] References Cited

U.S. PATENT DOCUMENTS 4,116,994 9/1978 Vannice et al. .
4,162,262 7/1975 Ellgen et al. .
4,199,522 4/1980 Murchison et al. .
4,224,236 9/1980 Wunder et al. .
4,327,190 4/1982 Ball et al. .

FOREIGN PATENT DOCUMENTS 4656 10/1979 European Pat. Off. .
10295 4/1980 European Pat. Off. .

OTHER PUBLICATIONS

Ichikawa I, Bull. of Chem. Soc. of Japan, 51 (8), 2273-2277, 1978.
Ichikawa II, J.C.S. Chem. Comm. 1978, pp. 566-567.

Primary Examiner—Howard T. Mars
Attorney, Agent, or Firm—Wenderoth, Lind & Ponack

[57] ABSTRACT

In a process for producing an oxygen-containing hydrocarbon compound having 1 or 2 carbon atoms which comprises reacting a gaseous mixture of a carbon oxide and hydrogen in the presence of a hydrogenation catalyst, the improvement wherein said hydrogenation catalyst is a catalyst composition comprising (A) substantially metallic rhodium and
(B) an oxide of a metal selected from the group consisting of metals of Groups IIa, IIIa, IVa and Va of the periodic table of short form, or (i) substantially metallic rhodium,
(ii) an element selected from the group consisting of niobium, tantalum, chromium, manganese and rhenium, and
(iii) an oxide of a metal selected from the group consisting of metals of Groups IIIa, IVa and Va of the periodic table of short form.

8 Claims, No Drawings

PROCESS FOR PRODUCING OXYGEN-CONTAINING HYDROCARBON COMPOUNDS

This application is a continuation of now abandoned application Ser. No. 348,193, filed Feb. 12, 1982, which is a continuation of now abandoned application Ser. No. 165,005, filed July 1, 1980.

This invention relates to a process for producing oxygen-containing hydrocarbon compounds having 1 or 2 carbon atoms by reacting a gaseous mixture composed of carbon oxide and hydrogen in the presence of a hydrogenation catalyst. More specifically, this invention pertains to a process for advantageously producing oxygen-containing hydrocarbon compounds having 1 or 2 carbon atoms, particularly ethanol, from the aforesaid gaseous mixture using a catalyst composition comprising metallic rhodium and a certain metallic oxide as a hydrogenation catalyst.

In recent years, there has been a worldwide scarcity of oil resources, and it is anticipated that a balance between supply and demand of oils will be aggravated in the near future. Naphtha derived from crude oils has become increasingly costly in recent years, and the cost of production of low-boiling olefins, acetic acid, acetaldehyde, ethanol, etc., which are the basic products of the petrochemical industry from naphtha, has tended to increase year by year. Accordingly, there has been an increasing need to develop a process for producing these basic raw materials of the petrochemical industry at low cost from a synthesis gas comprising a mixture of carbon monoxide and hydrogen.

Presently, the synthesis gas is produced industrially by steam-reforming of naphtha and natural gases, but it is expected that in the near future synthesis gases from low-cost carbon resources occurring abundantly throughout the world such as heavy oils, coals and oil sands will go into industrial production. The synthesis gas will therefore be an advantageous raw material both in cost and supply.

Extensive investigations have been made heretofore about the production of hydrocarbons or both hydrocarbons and oxygen-containing hydrocarbon compounds from a gaseous mixture of carbon oxide (carbon monoxide or carbon dioxide) and hydrogen (a synthesis gas process or a modified Fischer-Tropsch method). It has been reported, for example, that various oxygen-containing hydrocarbon compounds and hydrocarbons can be synthesized by reacting a synthesis gas comprising carbon monoxide and hydrogen in a ratio of from 4:1 to 1:4 in the presence of a hydrogenation catalyst comprising a metal of the iron group or noble metal group at a temperature of 150° to 450° C. and a pressure of 1 to about 700 atmospheres [F. Fisher, H. Tropsch, Ber., 59,830, 832, 923 (1926), and H. Pichler, Adv. Catalysis, IV, 271 (1952)]. The product obtained by this method is a mixture of oxygen-containing hydrocarbon compounds and hydrocarbons having 1 to 20 carbon atoms, and this method cannot afford industrially useful oxygen-containing hydrocarbon compounds having low carbon numbers selectively and efficiently.

As a method for synthesizing oxygen-containing hydrocarbon compounds and lower olefins from a synthesis gas, the Hydrocol method comprising performing the reaction at 300° to 350° C. and 20 to 50 atmospheres using a catalyst composed of iron or cobalt supported on magnesium oxide, thorium oxide, etc. [see H. Pichler, Adv. Catalysis IV, 271 (1952)], and the Synthol method involving performing the reaction at 300° to 400° C. and 70 to 250 atmospheres [F. Fischer, H. Tropsch, Brennstoff-Chem. 4, 276 (1923), 5, 201, 217 (1924), 7, 97, 299 (1926), 8, 165 (1927)] have already been known. These methods, however, have poor selectivity. They are advantageous for production of higher olefins, but cannot selectively give olefins having 2 to 4 carbon atoms and oxygen-containing hydrocarbon compounds having 1 or 2 carbon atoms which are useful as industrial materials.

On the other hand, as regards the use of a rhodium catalyst, a method was suggested which comprises contacting a synthesis gas at atmospheric pressure with a rhodium-supported catalyst containing a silica or alumina carrier or a rhodium metal plate to produce methane and not more than 10% of $C_2$-$C_4$ hydrocarbons [see M. A. Vannice, J. Catal., 37, 449 (1975), and B. Sexton, G. A. Somorjai, ibid. 46, 167 (1977)]. Furthermore, about the selective production of oxygen-containing hydrocarbon compounds having low carbon numbers by reaction of a synthetic gas using a rhodium-supported catalyst, there were proposed a method which comprises reacting a synthetic gas at 290° to 325° C. and 35 to 350 atmospheres while maintaining the $CO/H_2$ ratio at much higher than 1 and the flow rate of the reactant gas at $10^3 h^{-1}$ or higher as SV, to produce a mixture of oxygen-containing hydrocarbon compounds having low carbon numbers, especially acetic acid, acetaldehyde and ethanol, in a carbon efficiency, based on the consumed carbon monoxide, of 50% (Belgian Pat. No. 824822, DT No. 2503233, and Japanese Laid-Open Patent Publication No. 80806/76); and a method which comprises reacting a synthesis gas at a flow rate of at least $10^3 h^{-1}$ under a pressure of 50 to 300 atmospheres using a silica carrier catalyst containing rhodium and iron to produce methanol and ethanol at substantially the same carbon efficiency as in the aforesaid method (see Belgian Pat. No. 824823, and Japanese Laid-Open Patent Publication No. 80807/76). These methods give methanol and ethanol in a substantially equimolar ratio, but cause formation of large amounts of methane or hydrocarbons having 2 or more carbon atoms as by-products. At a low CO concentration in the synthesis gas ($CO/H_2 = 1.0$ or less), a low pressure (1 to 50 atmospheres) or a low flow rate (not more than $10^2 h^{-1}$ as SV) which are advantageous conditions for economical industrial processes, by-product hydrocarbons tend to increase further in these methods, and the selectivity for industrially useful oxygen-containing hydrocarbon compounds having 1 or 2 carbon atoms such as ethanol is drastically reduced.

According to an improved method involving use of a catalyst comprising both rhodium and manganese (see Japanese Laid-Open Patent Publication No. 14706/77), an increase in the conversion of CO per unit weight of rhodium is noted, but the addition of manganese can scarcely increase the selectivity for the formation of oxygen-containing hydrocarbon compounds. It has been pointed out that the addition of an excessive amount of manganese rather increases formation of hydrocarbons and reduces the selectivity for the formation of the desirable oxygen-containing hydrocarbon compounds.

A method has also been known for producing a mixture of methanol and ethanol from a synthesis gas by reacting it at 1 to 50 atmospheres and 150° to 300° C. using a catalyst obtained by supporting a rhodium cluster or platinum cluster on an oxide of at least one metal selected from metals of Groups IIab, IIIab and IVab of the periodic table of short form (see Japanese Laid-Open Patent Publications Nos. 41291/79 and 44605/79). Although the catalyst used in this method is highly active, this method still has various difficulties which have to be overcome. For example, catalyst preparation requires the use of a special and expensive noble metal carbonyl cluster compound as a raw material, and includes operation in an inert atmosphere (in vacuum or in an inert gas). The catalyst has a short lifetime under high-temperature and high-pressure conditions which are required for achieving a high conversion, and there is a limit to the operable temperature range for the catalyst.

In view of the prior art techniques discussed above, it has been desired to develop a rhodium-containing catalyst which is suitable for selective production of oxygen-containing hydrocarbon compounds having 1 or 2 carbon atoms, particularly ethanol, at a high carbon efficiency under relatively mild low-pressure reaction conditions. The use of such a rhodium-containing catalyst will provide a new technique which supersedes synthesis of methanol from a synthesis gas or production of ethylene from naphtha.

It is an object of this invention to provide a process for producing oxygen-containing hydrocarbon compounds having 1 or 2 carbon atoms at a high carbon efficiency from a gaseous mixture of carbon oxide and hydrogen using a rhodium-containing catalyst which is relatively inexpensive and is easily available.

Another object of this invention is to provide a process for producing oxygen-containing hydrocarbon compounds having 1 or 2 carbon atoms, especially ethanol, from a gaseous mixture of carbon oxide and hydrogen.

Other objects and advantages of this invention will become apparent from the following description.

It has now been found in accordance with this invention that when a catalyst composition consisting basically of (A) substantially metallic rhodium and (B) an oxide of a metal (to be referred to as a "metal oxide") selected from metals of Groups IIa, IIIa, IVa and Va of the periodic table of short form is used in the production of oxygen-containing hydrocarbon compounds by reacting a gaseous mixture composed of carbon oxide and hydrogen, the carbon efficiency of the oxygen-containing hydrocarbon compounds having 1 or 2 carbon atoms is markedly improved, and reaches 50% or more. It has also been found that the catalyst composition used in this invention generally has a wide operating temperature range, and exhibits superior catalytic activity at a wide temperature range of from about 100° to about 400° C., and its catalytic activity lasts for an extended period of time even under high-temperature, high-pressure reaction conditions.

According to one aspect of this invention, there is provided a process for producing oxygen-containing hydrocarbon compounds having 1 or 2 carbon atoms which comprises reacting a gaseous mixture consisting of carbon oxide and hydrogen in the presence of a hydrogenation catalyst, said hydrogenation catalyst being a catalyst composition comprising (A) substantially metallic rhodium, and
(B) an oxide of a metal selected from metals of Groups IIa, IIIa, IVa and Va of the periodic table of short form.

In the present specification and the appended claims, the term "oxygen-containing hydrocarbon compounds having 1 or 2 carbon atoms" denotes hydrocarbons having 1 or 2 carbon atoms and an oxygen atom, such as methanol, ethanol, formaldehyde, acetaldehyde, formic acid and acetic acid.

The term "carbon oxide" inclusively represents both carbon monoxide (CO) and carbon dioxide ($CO_2$). In the present invention carbon monoxide and carbon dioxide are used either singly or as a mixture. Preferably, the carbon oxide is carbon monoxide.

The "periodic table of short form", as used in the present application, denotes a periodic table of the type described at page 738 of "Encyclopaedia Chimica", Vol. 5 (1951), Kyoritsu Shuppan K.K., Tokyo, Japan. According to this periodic table, Group IIa includes Be, Mg, Ca, Sr, Ba and Ra; Group IIIa, Sc, Y, lanthanide elements and actinide elements; Group IVa, Ti, Zr and Hf; and Group Va, V, Nb and Ta.

The term "carbon efficiency of oxygen-containing hydrocarbon compounds", as used in this application, denotes the percentage of the oxygen-containing hydrocarbon compounds in moles based on the consumed carbon oxide calculated for carbon (on the carbon basis).

The term "selectivity for ethanol", as used in this application, denotes the percentage of ethanol based on the resulting oxygen-containing hydrocarbon compounds calculated for carbon (on the carbon basis).

The metallic oxide used in the catalyst composition in accordance with this invention is an active catalytic ingredient having the ability to increase synergistically the catalytic activity of metallic rhodium which is a main catalytic ingredient. At the same time, the metal oxide serves as a carrier for metallic rhodium. The catalyst composition preferably consists essentially of metallic rhodium and the aforesaid metal oxide.

Examples of the metal oxide include magnesium oxide, calcium oxide, beryllium oxide, lanthanum oxide, cerium oxide, neodymium oxide, yttrium oxide, zirconium oxide, titanium oxide, thorium oxide, vanadium oxide, niobium oxide and tantalum oxide. Of these, lanthanium oxide, neodymium oxide, cerium oxide, yttrium oxide, thorium oxide, titanium oxide, zirconium oxide, niobium oxide, and tantalum oxide are preferred. Thorium oxide, titanium oxide, zirconium oxide, niobium oxide and tantalum oxide are especially preferred.

These metal oxides can be used either singly or in combination with each other. In order to support metallic rhodium, the metal oxide may generally be a solid in the form of powder, granule, pellet or lump having a surface area of generally at least 1 m²/g, preferably 10 to 1000 m²/g.

Deposition of metallic rhodium on the metal oxide can be effected by any customary method so long as substantially all of the rhodium deposited on the metal oxide is metallic. Advantageously, this can be performed using a single organic or inorganic salt of rhodium. The "simple salt of rhodium", as referred to herein, means a compound simply containing mono- or di-nuclear rhodium element, and is clearly distinct from the cluster compound of rhodium mentioned hereinabove. Specific examples of the simple salt of rhodium include inorganic salts of rhodium such as the chloride, nitrite and carbonate of rhodium, and organic salts of rhodium such as the acetate, oxalate, ethylenediamine complex [Rh($NH_2C_2H_4NH_2$)$_3$]Cl$_3$, pyridine complex [Rh($C_4H_4N$)$_4$Cl$_3$], acetylacetonate salt, cyclooctadiene complex, dicyclopentadienyl complex, π-allyl complex, and allene complex of rhodium.

Deposition of metallic rhodium on the metal oxide from these rhodium salts may be performed, for example, by a method which comprises dissolving the rhodium salt in a suitable solvent (for example, water, an alcohol such as methanol or ethanol, an ether such as tetrahydrofuran or dioxane, or a hydrocarbon such as hexane or benzene), impregnating the metal oxide with the resulting solution, removing the solvent, and then heat-treating the impregnated metal oxide in an atmosphere of a reducing gas such as hydrogen gas or synthesis gas under atmospheric or elevated pressures until substantially all of the impregnated rhodium salt is converted to metallic rhodium (for example, at a temperature of about 50° to about 500° C. for about 10 minutes to about 2 days; this reducing treatment can be performed in a reactor prior to the performance of the process of this invention); or chemically reducing the impregnated metal rhodium salt with a reducing agent such as formaldehyde, hydrazine, metal hydrides (e.g., sodium hydride or potassium hydride), metal borohydrides (e.g., sodium borohydride), or complex metal hydrides (e.g., lithium aluminum hydride). As a result, there can be obtained a catalyst composition in accordance with this invention in which substantially metallic rhodium is supported and combined with the metal oxide.

The content of metallic rhodium is not critical, and can be widely varied depending upon the type or shape of the metal oxide used, etc. Generally, it is advantageous that the content of metallic rhodium is about 0.0001 to about 50% by weight, preferably about 0.01 to about 25% by weight, more preferably about 0.1 to about 10% by weight, based on the weight of the catalyst composition.

The catalyst composition consisting essentially of metallic rhodium and the metal oxide so prepared can be directly used in the process of this invention.

It has further been found in accordance with this invention that the carbon efficiency of the oxygen-containing hydrocarbon compound having 1 or 2 carbon atoms and the selectivity for ethanol can be further improved by incorporating an element selected from niobium, tantalum, chromium, manganese and rhenium as a sub-main catalyst ingredient into a catalyst composition consisting of metallic rhodium and an oxide of a metal selected from metals of Groups IIIa, IVa and Va of the periodic table of short form, and using the resulting catalyst composition in the reaction of a gaseous mixture of hydrogen and carbon oxide.

Thus, according to another aspect of this invention, there is also provided a process for producing oxygen-containing hydrocarbon compounds having 1 or 2 carbon atoms which comprises reacting a gaseous mixture composed of carbon oxide and hydrogen in the presence of a hydrogenation catalyst, said hydrogenation catalyst being a catalyst composition comprising (i) substantially metallic rhodium, (ii) an element selected from the group consisting of niobium, tantalum, chromium, manganese and rhenium, and (iii) an oxide of a metal selected from the group consisting of metals of Groups IIIa, IVa and Va of the periodic table of short form.

The catalyst composition used in this process can be prepared in the same way as the aforesaid catalyst composition except that the metal element selected from niobium, tantalum, chromium, manganese and rhenium is additionally deposited on the metal oxide.

Deposition of such additional metal element on the metal oxide can be performed in the same way as in the deposition of metallic rhodium. For example, it can be performed by dissolving an inorganic or organic salt or alkoxide of the metal element in a suitable solvent (for example, water, an alcohol such as methanol or ethanol, an ether such as tetrahydrofuran or dioxane, or a hydrocarbon such as hexane or benzene), impregnating the resulting solution in the metal oxide, removing the solvent, and reducing the impregnated metal salt until substantially all of it is reduced to metallic element as in the case of metallic rhodium.

The inorganic or organic salt or alkoxide of the additional metal element that can be used includes the chlorides, nitrates, carbonates, acetates, oxalates, acetylacetonate salts, dicyclopentadienyl complexes, π-allyl complexes, allene complexes and alkoxides of the metals. Specific examples include rhenium chloride ($ReCl_5$), rhenium bromide ($ReBr_5$), rhenium carbonyl $[Re_2-(CO)_{10}]$, dicyclopentadienyl rhenium hydride $[(\pi-C_5H_5)-ReH_3]$, carbonyl dicyclopentadienyl rhenium $[(\pi-C_5H_5)-Re(CO)_2]$, rhenium nitrate $[Re(NO_3)_5.6H\ O]$, rhenium acetate $[Re(CH_3COO)_5]$, ammonium rhenate $[(NH_4)_2Re_2O_4]$, niobium chloride ($NbCl_5$), niobium bromide ($NbBr_5$), dicyclopentadienyl niobium hydride $[(\pi-C_5H_5)_2NbH_3]$, π-allyl niobium $[(\pi-C_3H_5)_4Nb]$, tantalum chloride ($TaCl_5$), tantalum bromide ($TaBr_5$), dicyclopentadienyl tantalum hydride $[(\pi-C_5H_5)_2TaH_3]$, π-allyl tantalum $[(\pi-C_3H_5)_4Ta]$, niobium acetylacetonate $[Nb(C_5H_7O_2)_5]$, tantalum acetylacetonate $[Ta(C_5H_7O_2)_5]$, manganese chloride ($MnCl_2.4H_2O$), manganese acetylacetonate $[Mn(C_5H_7O_2)_2]$, manganese acetate $[Mn(CH_3-COO)_2.4H_2O)$, manganese nitrate $[Mn(NO_3)_2.6H_2O]$, dicyclopentadienyl manganese $[(C_5H_5)_2Mn)$, chromium chloride ($CrCl_3$, or $CrCl_3.6H_2O$), chromium nitrate $[Cr(NO_3)_3.9H_2O]$, chromium acetylacetonate $[Cr(C_5H_7O_2)_3]$, dicyclopentadienyl chromium $[Cr(C_5H_5)_2]$, and π-allyl chromium $[(\pi-C_3H_5)_3Cr]$. These metal compounds can be used either singly or in combination with each other.

Deposition of such a metal element can be performed either before, during or after the deposition of metallic rhodium.

The amount of the metal element to be deposited is not critical, and can be varied widely depending upon the type of the metal element, etc. Generally, it is such that the weight ratio of metallic rhodium to the metal element is from 50:1 to 1:50, preferably from 20:1 to 1:20, more preferably from 1:10 to 10:1. The total amount of metallic rhodium and the metal element may be about 0.001 to about 50% by weight, preferably about 0.01 to about 25% by weight, more preferably about 0.1 to about 25% by weight, based on the weight of the catalyst composition.

The reaction of a gaseous mixture of carbon oxide and hydrogen in the presence of the catalyst composition of the various embodiments described hereinabove can be performed in a manner known per se. For example, the reaction can be performed by feeding the catalyst composition into a suitable catalytic reactor such as a closed circulating reactor, a fixed bed type reactor adapted for flowing of a starting gaseous mixture at atmospheric or elevated pressure, a batchwise pressure reactor or a batchwise shaking pressure reactor, and contacting the starting gaseous mixture with the catalyst composition at about 50° to about 450° C. and a space velocity of about 10 to about $10^6$ liters/liter.hr$^{-1}$, preferably about $10^2$ to about $10^5$ liters/liter.hr$^{-1}$, at a temperature of about 100° to about 350° C., and a pressure of about 0.5 to about 350 atmospheres (G), preferably about 1 to about 300 atmospheres (G).

The mole ratio of carbon oxide to hydrogen in the starting gaseous mixture to be fed into the reactor is generally from 20:1 to 1:20, preferably from 1:5 to 5:1, more preferably from 1:2 to 2:1.

Thus, according to the process of this invention, oxygen-containing hydrocarbon compounds having 1 or 2 carbon atoms can be produced with a high carbon efficiency from a gaseous mixture of carbon oxide and hydrogen by using the aforesaid catalyst composition which is easily available commercially and has excellent catalytic activity and selectivity. The process of this invention gives oxygen-containing hydrocarbon compounds containing methanol and/or ethanol as main ingredients. The mixture of methanol and ethanol formed as main ingredients can be easily separated into the constituents by distillation. Hence, the process of this invention is commercially feasible for production of methanol and ethanol. Moreover, blending of the oxygen-containing hydrocarbon compounds containing methanol and ethanol as main ingredients with a fuel gas gives fuels which may supersede the present fuels from natural resources and are expected to contribute to saving of petroleum resources.

One great advantage of the process of this invention is that ethanol can be produced at a high selectivity when the aforesaid catalyst composition further includes a metal element selected from niobium, tantalum, chromium, manganese and rhenium in addition to metallic rhodium.

Ethanol can be easily separated from the oxygen-containing hydrocarbon compounds containing a major proportion of ethanol which are obtained by the process of this invention. Hence, the process of this invention is commercially feasible for production of ethanol from a synthesis gas. Moreover, blending of the oxygen-containing hydrocarbon compounds containing ethanol as a main ingredient with a fuel gas or gasoline gives fuels which may supersede the present fuels from natural resources and are expected to contribute to saving of petroleum resources.

The following examples specifically illustrate the present invention. It should be noted however that the present invention is in no way limited by these examples.

The various abbreviations and terms appearing in the following examples have the following meanings.

*RG:* Reagent grade
*SV:* Space velocity defined as follows:

$$SV = \frac{\text{Amount of the feed gas (ml/hr)}}{\text{Amount of catalyst (ml)} \times \text{time (hr)}}$$

Feed: Amount of feed gas (ml/hr)
$C_1$: methane
$C_2$: ethane + ethylene
$C_3$: propane + propylene
$C_4$: butane + butene
*Tr:* Trace amount
*CE:* carbon efficiency (%) of oxygen-containing hydrocarbon compounds defined as follows:

-continued
$$CE = \frac{\begin{array}{c}\text{Moles of methanol + (moles of ethanol) + moles} \\ \text{of acetaldehyde + moles of acetic acid)} \times 2 + \\ \text{(moles of propanol)} \times 3 + \\ \text{(moles of butanol)} \times 4\end{array}}{\text{Moles of carbon oxide reacted}} \times 100$$

Selectivity for ethanol (%):

$$\frac{\text{(moles of ethanol formed)} \times 2}{\begin{array}{c}\text{Moles of the oxygen-contain-} \\ \text{ing hydrocarbon compounds} \\ \text{formed (on carbon basis)}\end{array}} \times 100$$

*STY:* Space time yield
STY of the oxygen-containing hydrocarbon compounds is expressed by the following equation.

$$STY = \frac{\begin{array}{c}\text{Weight of the oxygen-containing} \\ \text{hydrocarbon compounds (grams)}\end{array}}{\begin{array}{c}\text{(weight of the catalyst} \times \text{time (hours)} \\ \text{charged (kg))}\end{array}}$$

EXAMPLE 1

Rhodium chloride trihydrate (0.50 g) was dissolved in 100 cc of distilled water, and 20 g of magnesium oxide powder (RG; a product of Nakarai Chemical Co., Ltd.) was added to the aqueous solution to impregnate the magnesium oxide with the aqueous solution. The impregnated magnesium oxide was evaporated to dryness by a rotary evaporator to afford a yellow powder. The resulting yellow powder was packed into a closed circulating-type reactor (total capacity 400 ml), heat-treated under vacuum at 200° C., and then subjected to reducing treatment in a stream of hydrogen at 350° C. for 15 hours. After reduction, a gaseous mixture consisting of carbon monoxide and hydrogen was introduced into the reactor and the reaction was started under the conditions shown in Table 1 (this reaction will be referred to hereinbelow as a CO—H$_2$ reaction). When the activity of the catalyst became steady, the distribution of products of the CO—H$_2$ reaction was examined. The results are shown in Table 1.

EXAMPLES 2 TO 10

By the same operation as in Example 1, rhodium was deposited on 20 g of titanium oxide powder (a product of Merck; RG), zirconium oxide powder (a product of Nakarai Chemical Co., Ltd.; RG), lanthanum oxide powder (a product of Kishida Cheic Cheic Chemical Co., Ltd.; RG), neodymium oxide powder (a product of Wako Pure Chemical Co., Ltd.; RG), cerium oxide powder (99% pure, a product of Wako Pure Chemical Co., Ltd.), yttrium oxide powder (a product of Wako Pure Chemical Co., Ltd.; Rg), thorium oxide powder (a product of Tokyo Chemical Co., Ltd.; RG), niobium oxide powder (a product of Wako Pure Chemical Co., Ltd; RG), and tantalum oxide powder, respectively, using an aqueous solution of 0.50 g of rhodium chloride trihydrate in 100 cc of distilled water. Using the resulting catalysts, the CO—H$_2$ reaction was performed in the same way as in Example 1. The results are shown in Table 1.

The products in vapor phase were analyzed by gas chromatography using a thermal conducting detector (TCD) and an active column (1 m, room temperature, and an Al$_2$O$_3$-dimethylformamide (supported in an amount of 38% by weight) column (4 m, room temperature). The oxygen-containing hydrocarbon compounds trapped by a dry ice acetone trap of the reactor were analyzed to TCD gas chromatography on a Porapak Q (trademark) column (4 m, 200° C.) and a PEG-1500 column (2 m, 80° C.).

COMPARATIVE EXAMPLE 1

In the same way as in the preceding Examples, rhodium was deposited on 20 g of silica (WAKOW-GEL, 200 m$^2$/g, C-200) and γ-alumina (Nishio Kogyo K.K., 280 m$^2$/g, A-11), and using the resulting catalyst, the CO—H$_2$ reaction was performed in the same way as in the preceding Examples. The results are shown in Table 1.

It is seen that with the rhodium on silica or an γ-alumina, oxygen-containing hydrocarbon compounds were not formed, or formed only in traces.

resulting oxygen-containing hydrocarbon compounds were bubbled through two traps containing 200 ml of water, and the absorbed oxygen-containing hydrocarbon compounds were quantitatively and qualitatively analyzed by FID (flame ionization detector) gas-chromatography. The results are shown in Table 2.

EXAMPLE 12

Rhodium nitrate hydrate [Rh(NO$_3$)$_3$.xH$_2$O] (1.25 g) was dissolved in 100 ml of water, and 20 g of zirconium oxide powder (99.9% pure; a product of Nakarai Chemical Co., Ltd.) was added to the resulting solution to impregnate the powder with the aqueous solution. The impregnated zirconium oxide was dried by a rotary evaporator under reduced pressure, and pelletized by a

TABLE 1

| Example | Catalyst | Reaction conditions Temperature (°C.) | Partial pressure (mmHg) CO | Partial pressure (mmHg) H$_2$ | Time (hours) | CH$_3$OH | C$_2$H$_5$OH | CH$_3$CHO | Other oxygen-containing hydrocarbon compounds (*1) | C$_1$ | Other hydrocarbons (*2) | CE (%) |
|---|---|---|---|---|---|---|---|---|---|---|---|---|
| 1 | MgO—Rh (Rh 0.20 g) | 245 | 20 | 45 | 23 | 0.66 | 0.28 | — | — | 0.91 | 0.11 | 52 |
|  |  | 240 | 30 | 32 | 23.5 | 0.78 | 0.084 | — | — | 0.65 | 0.14 | 50 |
|  |  | 260 | 30 | 35 | 48 | 0.88 | 0.134 | — | — | 0.82 | 0.23 | 46 |
| 2 | TiO—Rh (Rh 0.20 g) | 210 | 20 | 45 | 48 | ± | 0.28 | 0.28 | + | 0.70 | 0.41 | 34 |
|  |  | 232 | 32 | 33 | 14 | ± | 0.23 | 0.15 | + | 0.46 | 0.27 | 43 |
| 3 | ZrO$_2$—RhCl$_3$ (Rh 0.20 g) | 185 | 20 | 45 | 48 | 0.23 | 0.37 | 0.086 | + | 0.422 | 0.06 | 66 |
|  |  | 200 | 30 | 35 | 39 | 0.184 | 0.32 | 0.22 | 0.013 | 0.63 | 0.176 | 56 |
| 4 | La$_2$O$_3$—Rh (Rh 0.20 g) | 235 | 20 | 45 | 6.8 | 0.53 | 0.19 | + | — | 0.49 | 0.25 | 43 |
|  |  | 202 | 20 | 45 | 23.5 | 0.51 | 0.085 | + | — | 0.44 | 0.02 | 59 |
|  |  | 198 | 20 | 45 | 47.5 | 1.23 | 0.17 | + | — | 0.57 | 0.08 | 68 |
| 5 | Nd$_2$O$_3$—Rh (Rh 0.20 g) | 198 | 20 | 45 | 43 | 1.58 | 0.28 | + | — | 0.52 | 0.04 | 75 |
|  |  | 220 | 20 | 45 | 18 | 0.67 | 0.18 | + | — | 0.85 | 0.21 | 45 |
| 6 | CeO$_2$—Rh (Rh 0.20 g) | 210 | 20 | 45 | 15 | 0.27 | 0.14 | 0.03 | 0.01 | 0.67 | 0.23 | 34 |
|  |  | 190 | 20 | 45 | 23 | 0.34 | 0.18 | 0.01 | 0.01 | 0.48 | 0.15 | 49 |
| 7 | Y$_2$O$_3$—Rh (Rh 0.20 g) | 220 | 20 | 45 | 14 | 0.51 | 0.15 | 0.01 | + | 0.79 | 0.21 | 37 |
|  |  | 195 | 20 | 45 | 46 |  | 1.06 | 0.08 | — | 0.59 | 0.10 | 57 |
| 8 | ThO$_2$—Rh (Rh 0.20 g) | 185 | 20 | 45 | 15 | 0.16 | 0.18 | 0.01 | + | 0.48 | 0.06 | 43 |
|  |  | 210 | 30 | 30 | 23 | 0.13 | 0.24 | 0.02 | + | 0.54 | 0.10 | 44 |
| 9 | Nb$_2$O$_5$—Rh (Rh 0.20 g) | 195 | 20 | 45 | 15 | 0.02 | 0.12 | 0.03 | 0.01 | 0.59 | 0.06 | 30 |
|  |  | 210 | 20 | 45 | 19 | 0.01 | 0.20 | 0.03 | 0.02 | 0.98 | 0.19 | 26 |
| 10 | Ta$_2$O$_5$—Rh (Rh 0.20 g) | 195 | 20 | 45 | 25 | 0.08 | 0.16 | 0.02 | + | 0.54 | 0.16 | 32 |
|  |  | 210 | 20 | 45 | 12 | 0.02 | 0.24 | 0.02 | + | 0.69 | 0.24 | 30 |
| Comparative Example 1 | γ-Al$_2$O$_3$—Rh (Rh 0.20 g) | 220 | 20 | 45 | 23 | — | — | — | — | 0.45 | 0.13 | —0 |
|  | SiO$_2$—Rh (Rh 0.20 g) | 235 | 20 | 42 | 48 | 0.01 | 0.03 | 0.04 | + | 0.38 | 0.15 | 17 |

Note 1: Other oxygen-containing hydrocarbon compounds include acetic acid and traces of propanol and butanol.
Note 2: Other hydrocarbons consist of C$_2$-C$_4$ hydrocarbons. Furthermore, about 0.01 to 0.1 millimole of CO$_2$.

EXAMPLE 11

Rhodium chloride trihydrate (2.0 g) was dissolved in 100 ml of water, and the solution was impregnated in 30 g of lanthanum oxide powder (purity 99.9%; a product of Nakarai Chemical Co.; Ltd.). The impregnated lanthanum oxide was air-dried, and the resulting powder was molded into pellets having a size of about 6 to 10 mesh by a tabletting machine. The pellets were packed into a pressure fixed-bed type reactor (40 in diameter × 500 mm in length; lined with Hastelloy-C). Glass beads having a diameter of 2 to 3 mm were filled on the top and bottom of the catalyst layer. The catalyst was heated at 350° C. for 5 hours in a stream of hydrogen at atmospheric pressure, and a pressurized synthesis gas was passed through the catalyst layer under the conditions shown in Table 2, and the conversion and the distribution of the products were examined. The off gas was analyzed by TCD gas-chromatography on an active carbon column (1 m, room temperature), and an Al$_2$O$_3$-DMF column (4 m, room temperature). The tableting machine. The resulting pellets were packed into a high-pressure reactor, and reduced in a stream of hydrogen at 250° C. and 1 atmosphere. A gaseous mixture consisting of CO and H$_2$ in a mole ratio of 0.5 or 1.0 was introduced, and reacted at a temperature of 250° to 320° C. under a pressure of 10, 20 or 40 atmospheres. The conversion of CO and the distribution of the resulting products are shown in Table 2.

EXAMPLE 13

Rhodium chloride trihydrate (0.50 g) was deposited on 20 g of zirconium oxide (99.9%; a product of Nakarai Chemical Co., Ltd.) from its aqueous solution in the same way as in Example 1. After drying, the impregnated zirconium oxide was dried and molded into pellets having a size of 8 to 10 mesh. The pellets were packed into a high-pressure fixed bed reactor, and subjected to reducing treatment in a stream of hydrogen (1000 ml/min.) at 350° C. and 1 atmosphere for 5 hours.

Then the CO—$H_2$ reaction at an elevated pressure was performed in the reactor under the conditions shown in Table 2. The results are also shown in Table 2.

For comparison, the results obtained by using silica-Rh are also shown in Table 2.

ined. The products were analyzed in the same way as in Example 11. The results are shown in Table 3.

COMPARATIVE EXAMPLES 3 AND 4

For comparison, 1.25 g of rhodium chloride trihy-

TABLE 2

| | | Reaction conditions | | | Amounts of the products formed (mmole/hr) | | | | | | |
|---|---|---|---|---|---|---|---|---|---|---|---|
| Example | Catalyst | Pressure (kg/cm$^2$) Temperature (°C.) | CO/$H_2$ mole ratio | Flow rate (ml/min.) | $CH_3OH$ | $C_2H_5OH$ | $CH_3CHO$ | $CH_3COOH$ | $C_1$ | Other hydrocarbons (*) | CE (%) |
| 11 | $La_2O_3$—Rh (Rh 0.80 g) | 10 K 305° C. | 0.5 | 200 | 0.67 | 3.22 | 0.05 | 0.10 | 9.1 | 2.1 | 35.9 |
| | | 20 K 310° C. | 0.5 | 400 | 2.93 | 8.0 | 0.11 | 0.35 | 13.3 | 0.84 | 51.0 |
| | | 40 K 270° C. | 0.5 | 800 | 5.53 | 12.9 | 0.43 | 0.75 | 21.0 | 1.05 | 59.2 |
| 12 | $ZrO_2$—Rh (Rh 0.40 g) | 20 K 296° C. | 0.5 | 800 | 0.10 | 1.04 | 0.48 | + | 4.14 | 0.30 | 38.2 |
| | | 40 K 336° C. | 1.0 | 800 | 0.02 | 1.46 | 0.55 | 0.62 | 8.50 | 1.04 | 32.5 |
| 13 | $ZrO_2$Rh (Rh 0.20 g) | 10 K 275° C. | 0.5 | 800 | 0.75 | 0.64 | 0.17 | + | 3.84 | 0.23 | 34.9 |
| | | 20 K 294° C. | 0.5 | 800 | 0.83 | 1.27 | 0.30 | + | 8.7 | 0.31 | 29.7 |
| | | 40 K 275° C. | 0.5 | 800 | 0.62 | 0.43 | 0.16 | * | 2.40 | 0.14 | 39.5 |
| Comparative Example 2 | $SiO_2$—Rh (Rh 0.50 g) | 10 K 252° C. | 0.5 | 800 | 0.01 | 0.076 | 0.75 | 0.08 | 10.1 | 2.9 | 8.6 |
| | | 10 K 294° C. | 0.5 | 800 | 0.08 | 0.5 | 1.4 | 0.10 | 22.0 | 9.0 | 7.8 |
| | | 20 K 266° C. | 1.0 | 800 | 0.04 | 0.24 | 1.4 | 0.10 | 9.3 | 5.6 | 10.7 |
| | | 20 K 292° C. | 1.0 | 800 | 0.04 | 0.91 | 1.6 | 0.10 | 18.2 | 5.4 | 12.8 |

Note:
The other hydrocarbons consist of $C_2$—$C_4$ hydrocarbons. A small amount of $CO_2$ formed, but was not included in determining the carbon efficiency in this table.

EXAMPLE 14

Rhodium chloride trihydrate (1.25 g) and 0.56 g of manganese chloride tetrahydrate were dissolved in 100 ml of distilled water, and 40 g of pellets of zirconium oxide (2 mm in diameter×2 mm in length, surface area 50 m$^2$/g; a product of Strem Chemicals Co. Ltd) was added to the aqueous solution. The impregnated zirconium oxide was evaporated to dryness by a rotary evaporator, and packed into a flowing type reactor (made of a Pyrex glass having a size of 18 mm in diameter×350 mm in length. Glass beads having a diameter of 2 to 3 mm were packed on the top and bottom of the catalyst layer. The catalyst was subjected to reducing treatment in a gaseous mixture at atmospheric pressure of hydrogen and helium ($H_2$ 20 ml/min., He 40 ml/min.) at 350° C. for 15 hours. A gaseous mixture of CO and $H_2$ (diluted with He; total pressure 1 atmosphere) was passed through the catalyst layer, and reacted. The conversion of CO and the distribution of the products were examdrate was deposited on 40 g of zirconium oxide (surface area 50 m$^2$/g; a product of Strem Chemicals Co. Ltd.), followed by reduction with hydrogen at 350° C. for 15 hours to form a catalyst (A). Separately, an aqueous solution of 1.25 g of rhodium chloride trihydrate and 0.50 g of manganese chloride tetrahydrate was impregnated in silica pellets (10 to 20 mesh, surface area 100 m$^2$/g; a product of Japan Gasoline Chemical Company), followed by reducing treatment in a hydrogen stream at 350° C. for 15 hours, to form a catalyst (B).

The CO—$H_2$ reaction was performed under atmospheric pressure using the same reactor as used in Example 9 in the presence of catalyst (A) or (B). The results are shown in Table 3.

It is seen from a comparison of Example 14 with Comparative Examples 3 and 4 that by using a catalyst comprising zirconium oxide, rhodium and manganese, the selectivity for ethanol and the carbon efficiency of the oxygen-containing hydrocarbon compounds in the CO—$H_2$ reaction increase.

TABLE 3

| | | Feed gas (1 atm.) | | | Reaction temperature (°C.), |
|---|---|---|---|---|---|
| Example | Catalyst | CO (ml/min.) | $H_2$ (ml/min.) | He (ml/min.) | one-pass CO conversion (%) |
| 14 | Rh—Mn—$ZrO_2$ (Rh 0.50 g, Mn 0.15 g) | 20 | 40 | 20 | 212° C., 3.5% |
| | | 20 | 40 | 20 | 220° C., 8.0% |
| | | 25 | 50 | 20 | 212° C., 2.9% |
| Comparative Example 3 | Rh—$ZrO_2$ (catalyst A) (Rh 0.50 g) | 20 | 40 | 20 | 200° C., 1.7% |
| | | 20 | 40 | 20 | 212° C., 2.6% |
| | | 20 | 40 | 20 | 222° C., 5.3% |
| Comparative Example 4 | Rh—Mn—$SiO_2$ (catalyst B) (Rh 0.50 g, Mn 0.14 g) | 20 | 40 | 20 | 230° C., 0.32% |
| | | 20 | 40 | 20 | 260° C., 1.5% |
| | | 20 | 40 | 20 | 290° C., 4.8% |

EXAMPLE 20

Rhodium chloride trihydrate (1.25 g) and 0.50 g of manganese nitrate hexahydrate (a product of Wako Pure Chemical Co., Ltd.; 99% pure) were dissolved in 100 ml of water, and 40 g of pellets of zirconium oxide (2 mm in diameter × 2 mm; a product of Strem Chemical Co. Ltd) was impregnated with the aqueous solution. The impregnated zirconium oxide pellets were dried by evaporation in a rotary evaporator, and packed into a flow-type reactor made of a Pyrex glass, and subjected to reducing treatment in a stream of hydrogen [a mixture of $H_2$ (20 ml/min.) and He (40 ml/min.)] at 350° C. for 15 hours. A gaseous mixture of CO and $H_2$ was passed through the catalyst layer, and the reaction was started under the conditions shown in Table 5. The conversion of CO and the amounts of the products yielded per hour were examined, and the results are shown in Table 5.

TABLE 5

|  | Example 19 | | Example 20 | | |
|---|---|---|---|---|---|
| Catalyst | Rh—Re—$ZrO_2$ | | Rh—Mn—$ZrO_2$ | | |
|  | (Rh 0.36 g, Re 0.20 g) | | (Rh 0.50 g, Mn 0.10 g) | | |
| Feed Composition (ml/min. at 1 atm.) | | | | | |
| CO | 20 | 20 | 20 | 20 | 20 |
| $H_2$ | 40 | 40 | 40 | 40 | 40 |
| He | 20 | 20 | 20 | 20 | 20 |
| Reaction temperature (°C.), | 200° C. | 225° C. | 185° C. | 200° C. | 215° C. |
| One-pass CO conversion (%) | 2.6% | 3.5% | 0.8% | 3.2% | 7.4% |
| Amounts of the products (mmole/hr) (*) | | | | | |
| $CH_3OH$ | 0.006 | 0.007 | ± | — | — |
| $C_2H_5OH$ | 0.318 | 0.308 | 0.151 | 0.375 | 0.485 |
| $CH_3CHO$ | 0.006 | 0.010 | ± | 0.005 | 0.020 |
| $CH_3OOOH$ | ± | ± | ± | ± | ± |
| $C_1$ | 0.478 | 0.707 | 0.123 | 0.598 | 1.95 |
| $C_2$ | 0.036 | 0.109 | 0.002 | 0.032 | 0.12 |
| $C_3$ | 0.028 | 0.073 | 0.004 | 0.065 | 0.15 |
| $C_4$ | ± | ± | ± | ± | 0.02 |
| $CO_2$ | 0.060 | 0.062 | 0.002 | 0.047 | 0.12 |
| CE (%) | 48.9 | 35.3 | 68.3 | 45.6 | 26.3 |
| Ethanol selectivity (%) | 97.5 | 95 | 99 | 98 | 96 |

Note: Acetic acid was obtained as methanol and ethyl acetate. The ethyl groups of byproduct diethyl ether and ethyl acetate were included in the amount of ethanol.

EXAMPLE 21

A gaseous mixture of CO, $CO_2$ and $H_2$ was passed through the catalyst prepared in Example 16, and reacted under the conditions shown in Table 6. The amounts of the products yielded per hour are shown in Table 6.

TABLE 6

|  | Example 21 | |
|---|---|---|
| Catalyst | Rh—Nb—$ZrO_2$ | |
|  | (Rh 0.50 g, Nb 0.19 g) | |
| Reaction temperature (°C.) | 175 | 182 |
| Feed composition (ml/min.) | | |
| CO | 15 | 20 |
| $H_2$ | 40 | 40 |
| He | 20 | 20 |
| $CO_2$ | 5 | 5 |
| Amounts of the products (m-moles/hr) | | |
| $CH_3OH$ | — | — |
| $CH_3CHO$ | 0.05 | 0.05 |
| $C_2H_5OH$ | 0.38 | 0.57 |
| Diethyl ether | 0.02 | 0.03 |
| $CH_3COOH$ | 0.01 | 0.01 |
| $C_1$ | 0.46 | 0.81 |
| $C_2$ | 0.01 | 0.04 |
| $C_3$ | 0.02 | 0.03 |
| $C_4$ | ± | 0.01 |

EXAMPLE 22

Rhodium chloride trihydrate (1.25 g) and 0.50 g of rhenium chloride were dissolved in 100 ml of methanol. The resulting solution was impregnated in titanium oxide pellets (a product of Ishihara Sangyo K.K.; in the form of balls with a diameter of 2 to 3 mm, surface area 40 m²/g). The impregnated titanium oxide pellets were dried under reduced pressure, and subjected to reducing treatment at 350° C. for 15 hours in a gaseous mixture consisting of $H_2$ (20 ml/min.) and He (40 ml/min.) to prepare a catalyst. Using the resulting catalyst, the CO—$H_2$ reaction was carried out under atmospheric pressure by the same operation as in Example 14. The results are shown in Table 7.

EXAMPLES 23 AND 24

Rhodium chloride trihydrate (1.25 g) and 0.50 g of rhenium chloride were deposited from their methanol (100 ml) solution on 30 g of each of lanthanum oxide powder and thorium oxide (RG; a product of Kishida Chemical Co., Ltd.) by the same operation as in Example 22. The resulting supported product was pelletized by a tableting machine, and packed into a reactor. It was subjected to the same hydrogen reducing treatment as in Example 22 and then, the CO—$H_2$ reaction was performed using the resulting catalysts. The results are shown in Table 7.

TABLE 7

|  | Example 22 | | Example 23 | | Example 24 | |
|---|---|---|---|---|---|---|
| Catalyst | Rh—Re—$TiO_2$ | | Rh—Re—$La_2O_3$ | | Rh—Re—$ThO_2$ | |
|  | (Rh 0.50 g, Re 0.26 g) | | (Rh 0.50 g, Re 0.26 g) | | (Rh 0.50 g, Re 0.26 g) | |
| Feed composition (ml/min. at 1 atm.) | | | | | | |
| CO | 20 | 20 | 20 | 20 | 20 | 20 |
| $H_2$ | 40 | 40 | 40 | 40 | 40 | 40 |
| He | 20 | 20 | 20 | 20 | 20 | 20 |
| Reaction temperature (°C.), One-pass CO conversion (%) | 185° C. | 205° C. | 200° C. | 215° C. | 180° C. | 205° C. |
|  | 1.78% | 5.6% | 1.7% | 3.6% | 2.9% | 5.1% |
| Amounts of the products (mmoles/hr) | | | | | | |
| $CH_3OH$ | + | + | 0.175 | 0.205 | 0.032 | 0.015 |
| $C_2H_5OH$ | 0.211 | 0.581 | 0.152 | 0.310 | 0.286 | 0.459 |
| $CH_3CHO$ | 0.023 | 0.036 | 0.020 | 0.032 | + | 0.014 |
| $CH_3COOH$ | + | + | + | + | + | + |
| $C_1$ | 0.380 | 1.315 | 0.320 | 0.595 | 0.489 | 0.721 |

TABLE 3-continued

| | | Amounts of the products (m-moles/hr) (*) | | | | | | | | CE | Ethanol selectivity |
|---|---|---|---|---|---|---|---|---|---|---|---|
| Example | CH$_3$OH | C$_2$H$_5$OH | CH$_3$CHO | CH$_3$COOH | C$_1$ | C$_2$ | C$_3$ | C$_4$ | CO$_2$ | (%) | (%) |
| 14 | — | 0.382 | 0.004 | ± | 0.670 | 0.044 | 0.070 | ± | 0.057 | 43 | 99 |
| | — | 0.478 | 0.01 | ± | 2.13 | 0.11 | 0.26 | + | 0.13 | 23 | 98 |
| | — | 0.370 | 0.02 | ± | 0.820 | 0.034 | 0.094 | ± | 0.01 | 40 | 95 |
| Comparative Example 3 | — | 0.163 | 0.03 | ± | 0.374 | 0.1010 | 0.057 | + | 0.01 | 36 | 98 |
| | — | 0.164 | 0.05 | ± | 0.676 | 0.020 | 0.088 | + | 0.01 | 27 | 97 |
| | — | 0.260 | 0.02 | ± | 1.140 | 0.047 | 0.182 | 0.026 | 0.036 | 22 | 90 |
| Comparative Example 4 | — | 0.007 | 0.0015 | ± | 0.130 | 0.010 | ± | ± | ± | 10.1 | 82 |
| | — | 0.035 | 0.014 | + | 0.348 | 0.093 | 0.052 | ± | ± | 12.4 | 72 |
| | — | 0.031 | 0.032 | 0.001 | 1.27 | 0.28 | 0.166 | ± | 0.052 | 5.0 | 48 |

Note:
Acetic acid was obtained as ethyl acetate. The ethyl groups of diethyl ether formed as by-product and ethyl acetate were included in the amount of ethanol formed.

EXAMPLES 15 TO 18

Rhodium chloride trihydrate (1.25 g) and 0.5 to 0.6 g of rhenium chloride, niobium chloride, tantalum chloride or chromium chloride were dissolved in methanol, or ethanol. The resulting solution was impregnated in pellets of zirconium oxide (2 mm in diameter×2 mm, surface area 50 m$^2$/g; a product of Strem Chemicals Co. Ltd.). The solvent was then removed by drying under reduced pressure, and the impregnated zirconium oxide pellets were subjected to reducing treatment in a gaseous mixture of H$_2$ (20 ml/min.) and He (40 ml/min.) at 350° C. for 15 hours to prepare a catalyst. Using the resulting catalyst, the CO—H$_2$ reaction was carried out at atmospheric pressure by the same operation as in Example 14. The conversion of CO and the distribution of the products were examined, and are shown in Table 4.

EXAMPLE 19

Thirty grams of zirconium oxide (a product of Nakarai Chemical Co., Ltd; 99.9%, surface area 30 m$^2$/g) was dissolved in a solution of 0.90 g of rhodium chloride trihydrate and 0.40 g of rhenium chloride in 100 ml of methanol. The solvent was removed by drying under reduced pressure in a rotary evaporator to afford a reddish brown powder. The powder was pelletized by a tableting machine under a pressure of 350 kg/cm$^2$ to form pellets having a size of 10 to 20 mesh. The pelletized catalyst was packed into a flow-type reactor, and subjected to reducing treatment in a stream of hydrogen at 350° C. for 15 hours. Then, the CO—H$_2$ reaction was performed under atmospheric pressure. The results are shown in Table 5.

TABLE 4

| Example | Catalyst | Feed composition (1 atm.) | | | Reaction temperature (°C.), one-pass CO conversion (%) | |
|---|---|---|---|---|---|---|
| | | CO (ml/min.) | H$_2$ (ml/min.) | He (ml/min.) | | |
| 15 | Rh—Re—ZrO$_2$ (Rh 0.50 g, Re 0.26 g) | 20 | 40 | 20 | 182° C., | 1.7% |
| | | 20 | 40 | 20 | 193° C., | 3.8% |
| | | 40 | 40 | 0 | 205° C., | 2.5% |
| 16 | Rh—Nb—ZrO$_2$ (Rh 0.50 g, Nb 0.19 g) | 20 | 40 | 20 | 162° C., | 1.4% |
| | | 20 | 40 | 20 | 175° C., | 2.8% |
| | | 20 | 40 | 20 | 188° C., | 8.0% |
| 17 | Rh—Ta—ZrO$_2$ (Rh 0.50 g, Ta 0.27 g) | 20 | 40 | 20 | 180° C., | 1.2% |
| | | 20 | 40 | 20 | 195° C., | 5.5% |
| | | 20 | 40 | 20 | 210° C., | 7.6% |
| 18 | Rh—Cr—ZrO$_2$ (Rh 0.50 g, Cr 0.20 g) | 20 | 40 | 20 | 200° C., | 2.3% |
| | | 20 | 40 | 20 | 220° C., | 5.7% |
| | | 40 | 40 | 0 | 200° C., | 1.4% |

| | | Amounts of the products (mmoles/hr) (*) | | | | | | | | CE | Ethanol selectivity |
|---|---|---|---|---|---|---|---|---|---|---|---|
| Example | CH$_3$OH | C$_2$H$_5$OH | CH$_2$CHO | CH$_3$COOH | C$_1$ | C$_2$ | C$_3$ | C$_4$ | CO$_2$ | (%) | (%) |
| 15 | — | 0.293 | ± | ± | 0.249 | 0.004 | 0.009 | + | 0.005 | 67 | 99.9 |
| | — | 0.509 | 0.002 | — | 0.696 | 0.042 | 0.046 | + | 0.016 | 52 | 99 |
| | — | 0.610 | 0.003 | — | 1.000 | 0.050 | 0.07 | 0.007 | 0.007 | 48 | 99 |
| 16 | — | 0.250 | 0.030 | ± | 0.130 | + | 0.020 | ± | ± | 76 | 89 |
| | — | 0.435 | 0.046 | ± | 0.473 | 0.009 | 0.010 | 0.002 | ± | 65 | 90 |
| | — | 0.804 | 0.080 | ± | 1.300 | 0.042 | 0.220 | 0.090 | ± | 42.4 | 90 |
| 17 | — | 0.158 | 0.027 | 0.024 | 0.198 | 0.003 | 0.005 | ± | ± | 65.6 | 75.5 |
| | — | 0.394 | 0.055 | 0.046 | 0.700 | 0.078 | 0.276 | 0.052 | 0.003 | 34.3 | 79.6 |
| | — | 0.526 | 0.064 | 0.059 | 1.510 | 0.042 | 0.310 | 0.042 | 0.004 | 32.4 | 81 |
| 18 | — | 0.240 | 0.011 | + | 0.520 | 0.003 | 0.057 | + | — | 41.8 | 96 |
| | — | 0.370 | 0.017 | + | 1.660 | 0.036 | 0.160 | + | — | 26.0 | 96 |
| | — | 0.260 | 0.034 | + | 0.367 | 0.0002 | 0.0005 | ± | — | 61.3 | 88 |

Note:
Acetic acid was obtained as ethyl acetate. The ethyl groups of diethyl ether formed as by-product and ethyl acetate were included in the amount of ethanol.

TABLE 7-continued

|  | Example 22 | | Example 23 | | Example 24 | |
| --- | --- | --- | --- | --- | --- | --- |
| $C_2$ | 0.013 | 0.046 | 0.004 | 0.028 | 0.058 | 0.135 |
| $C_3$ | 0.018 | 0.066 | 0.008 | 0.022 | 0.089 | 0.170 |
| $C_4$ | 0.006 | 0.012 | 0.001 | 0.002 | 0.004 | 0.018 |
| $CO_2$ | 0.012 | 0.019 | 0.038 | 0.281 | 0.055 | 0.130 |
| CE (%) | 49 | 42 | 57 | 47 | 40 | 35 |
| Ethanol selectivity (%) | 90 | 94 | 58 | 70 | 95 | 96 |

What we claim is:

1. In a process for producing an oxygen-containing hydrocarbon compound having 1 or 2 carbon atoms which comprises reacting a gaseous mixture of a carbon oxide and hydrogen in the presence of a hydrogenation catalyst, the improvement wherein said hydrogenation catalyst is a catalyst composition consisting of
   (i) metallic rhodium,
   (ii) an elemental metal selected from the group consisting of niobium, tantalum, manganese and rhenium, and
   (iii) a catalytically active oxide of zirconium.

2. The process of claim 1 wherein said metallic rhodium is formed from a simple salt of rhodium.

3. The process of claim 1 wherein the amount of said metallic rhodium is about 0.0001 to about 50% by weight based on the weight of said catalyst composition.

4. The process of claim 1 wherein the weight ratio of metallic rhodium to said elemental metal is from 10:1 to 1:10.

5. The process of claim 1 wherein said reaction is carried out at a temperature of about 50° to about 450° C. and a pressure of about 0.5 to about 350 atmospheres (gauge) at a space velocity of about 10 to about $10^6$ liters/liter.hr$^{-1}$.

6. The process of claim 1 wherein the carbon oxide is carbon monoxide.

7. The process of claim 1 wherein the mole ratio of the carbon oxide to hydrogen is from 20:1 to 1:20.

8. The process of claim 1 wherein said elemental metal is selected from the group consisting of niobium, tantalum and rhenium.

* * * * *